United States Patent [19]

Haskell

[11] 4,076,595
[45] Feb. 28, 1978

[54] EXTRACTIVE DISTILLATION OF C$_4$ HYDROCARBONS WITH AN EXTRACTANT MIXTURE

[75] Inventor: Donald M. Haskell, Bartlesville, Okla.

[73] Assignee: Phillips Petroleum Company, Bartlesville, Okla.

[21] Appl. No.: 731,955

[22] Filed: Oct. 13, 1976

[51] Int. Cl.$^2$ .................. B01D 3/40; C07C 11/16
[52] U.S. Cl. ........................... 203/51; 203/56; 203/57; 203/58; 203/62; 203/63; 203/78; 203/80; 260/677 A; 260/681.5 R
[58] Field of Search ............... 203/56, 51, 57, 58, 203/62, 63, 54, 73, 78, 80; 260/681.5 R, 677 A

[56] References Cited

U.S. PATENT DOCUMENTS

| 2,357,028 | 8/1944 | Shiros et al. | 203/58 |
| 2,455,803 | 12/1948 | Pierotti | 203/51 |
| 2,506,858 | 5/1950 | Davidson | 203/58 |
| 3,070,518 | 12/1962 | Nelson et al. | 203/58 |
| 3,846,332 | 11/1974 | Croix | 203/58 |

Primary Examiner—Wilbur L. Bascomb, Jr.

[57] ABSTRACT

A mixture of methylethylsulfone and at least one compound from the group including methylethylketone, acetone, and tetrahydrofuran is employed as a selective solvent in extractive distillation process for separation of diolefins from olefins.

10 Claims, 1 Drawing Figure

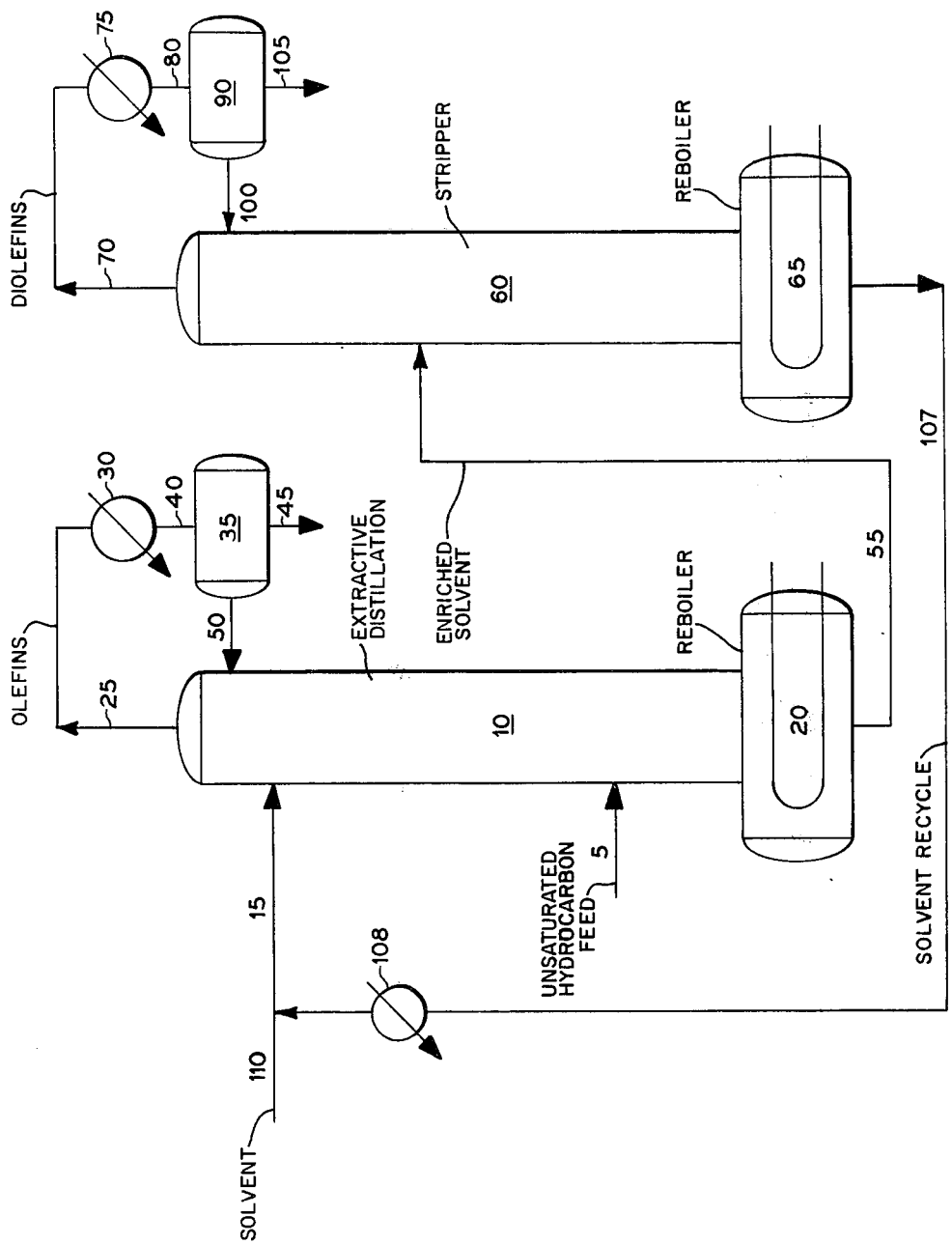

EXTRACTIVE DISTILLATION OF C$_4$ HYDROCARBONS WITH AN EXTRACTANT MIXTURE

BACKGROUND OF THE INVENTION

This invention relates to a separation process. In particular, it relates to separation of olefins from diolefins by extractive distillation.

Mixtures containing components of similar vapor pressures or components which tend to form azeotropes with one another are impossible to separate by simple distillation. Methods, such as azeotropic distillation, solvent extraction, adsorption on solids, and extractive distillation, have been proposed to achieve separation of these mixtures.

One separation which has caused considerable difficulty, is the separation of mixtures composed of olefins and diolefins, especially those having the same number of carbon atoms. To separate mixtures of olefins and diolefins, a third component, a selective solvent, can be added to the mixture to alter the relative volatility of the original constituents, thus permitting their separation. The term "relative volatility" ($\alpha$), an indicator of separability of a mixture by distillation, can be expressed for binary mixture as:

$$\alpha = \frac{y^*/(1-y^*)}{x/(1-x)} = \frac{y^*(1-x)}{x(1-y^*)}$$

where $x$ = mole fraction of A in the liquid, and
$y^*$ = mole fraction of A in vapor; A being the more volatile component.

When $\alpha = 1$, no separation is possible, and the larger the value of $\alpha$ above unity the greater the degree of separability. The selective solvent is usually of low volatility and is not appreciably vaporized in the fractionator. The selection of the solvent, for a particular system, is the crucial task in extractive distillation process.

The present invention provides a selective solvent for extractive distillation of a mixture comprising olefins and diolefins. Thus, one object of the invention is to provide an improved process for separation of mixtures of olefins and diolefins.

Another object of the invention is to provide a selective solvent for extractive distillation of a mixture including diolefins and olefins.

A further object of the invention is to provide an improved process for the removal of olefin impurities from a diolefin stream.

Still another object of the invention is to provide a solvent which is stable over wide range of temperatures.

Other objects of this invention will become apparent to those skilled in the art upon studying this disclosure.

SUMMARY OF THE INVENTION

A selective solvent comprising methylethylsulfone and at least one compound from a group including methylethylketone, acetone, and tetrahydrofuran, is employed in an extractive distillation process to separate diolefins from olefins.

In accordance with another aspect of the invention, the weight ratio of the selective solvent to the feed is in the range from about 2.0 to about 8.0, and the selective solvent includes about 55-85 weight percent of methylethylsulfone, and about 15-45 weight percent of methylethylketone or tetrahydrofuran. The solvent, when introduced to the extractive distillation column, alters the relative volatility of olefins to diolefins, thus permitting withdrawal of substantially pure olefin stream as overhead, and withdrawal of an extract stream containing mainly diolefin and the solvent. The solvent can then be separated from diolefin and recycled to the extractive distillation column.

In accordance with still another aspect of the invention, the selective solvent, comprising about 65-90 weight percent of methylethylsulfone, and about 10 to 35 weight percent of acetone, is added to a feed mixture of olefins and diolefins. The weight ratio of selective solvent to feed, in the range from about 2.0 to about 8.0, permits seaparation of feed mixture in a distillation zone into an overhead stream comprising essentially olefin and an extract stream comprising mainly diolefin and the solvent. Optionally, solvent can be separated from the diolefin and recycled to the extractive distillation column.

Other aspects of the invention will become apparent to those skilled in the art upon studying this specification and appended claims.

DETAILED DESCRIPTION OF THE INVENTION

Surprisingly, it was discovered that the presence of a selective solvent, composed of a mixture of methylethylsulfone and at least one solvent modifier from the group including methylethylketone, acetone, and tetrahydrofuran in the distillation zone of the extractive distillation column, allows for an improved separation of olefins from diolefins. Although the weight ratio of the selective solvent to the feed is usually in the range from about 2.0 to about 8.0, in some applications the ratio is outside this range. Those skilled in the art can easily determine the optimum amount for a given system.

The function of the solvent modifier is to improve the solubility of the selective solvent without adversely affecting the selective solvents' ability to alter the relative volatility of the feed components. In determining the optimum selective solvent composition for a given applciation, it has been found that it is preferred to select a composition that will provide a solubility to 10-40 weight percent for the major least soluble class of compounds at the temperature of the extractive distillation feed tray, and it is more narrowly preferred to operate at a solubility level of 20-30 weight percent. Thus, if the key separation is to be between butylenes and butadiene, the solvent composition should be selected which will provide a total butylene solubility of 10-40 weight percent at the feed tray temperature. The preferred solvent composition is further influenced by the relative amounts of the more unsaturated and less unsaturated components in the feed. Since the more unsaturated components are more soluble than the less unsaturated ones, it is generally desirable to operate in the lower end of the previously cited solubility range when the feed contains a major amount of the more unsaturated components. Otherwise, total hydrocarbon solubility would be so high through most of the column that selectivity of the solvent in the separation would be seriously impaired. The amount of methylethylsulfone in the selective solvent mixture usually varies from about 55 to about 85 weight percent when the solvent modifier is either methylethylketone or tetrahydrofuran, and varies from about 65 to about 90 weight percent when the solvent modifier is acetone.

The operating conditions of the column vary considerably depending on several factors including the constituents present in the mixture to be separated, the desired degree of separation, the number of trays in the column, and the composition of the selective solvent; however, the usual operating conditions for separating a $C_4$ hydrocarbon feed are as follows:

| Column | Pressure Range | | Temperature Range | | | |
|---|---|---|---|---|---|---|
| | | | Top | | Bottom | |
| | PSIA | KPa | °F | °C | °F | °C |
| Extractive Distillation | 55–115 | 379–793 | 80–140 | 27–60 | 210–285 | 99–141 |
| Stripper | 55–115 | 379–793 | 80–140 | 27–60 | 270–340 | 132–171 |

Internal reflux ratio in the extractive distillation column is in the range of 1.5–3.5; for the stripper it only need be adequate to separate solvent from the over head product.

The typical operating conditions for separating $C_4$ olefins and diolefins are shown below:

| Column | Pressure | | Top Temperature | | Reflux Ratio, |
|---|---|---|---|---|---|
| | PSIA | kPa | °F | °C | R/F (weight) |
| Extractive Distillation | 85 | 585 | 110 | 43 | 2.0 |
| Stripper | 85 | 585 | 110 | 43 | 0.1 |

The kettle temperatures will depend on the solvent composition, but for the usual selective solvent mixtures these will be about 210°–250° F (99°–121° C) for the extractive distillation column and 285°–325° F (141°–163° C) for the stripper. If butadiene is one of the components of the mixture to be separated, the temperature of both the extractive distillation and the stripper columns is desirably held in the lower end of the suggested ranges to minimize polymerization of butadiene during the distillation, and thus reduce the loss of this valuable component.

Since the solvent is selective for diolefinically unsaturated hydrocarbons as opposed to olefinically unsaturated hydrocarbons, the feed which is sought to be separated can contain olefins and diolefins having any number of carbon atoms. The invention is especially useful for separation of hydrocarbons having 4 or 5 carbon atoms. Both two-component and multi-component mixtures can be separated using the solvent of this invention. The feed to the extractive distillation column can also contain minor amounts of other hydrocarbons such as acetylenes and paraffins including propane, butanes and pentanes, without adversely affecting the operation of the system.

The practice of the invention will be further described by reference to a specific system depicted in the FIGURE. Referring now to the FIGURE, the feed containing olefinically and diolefinically unsaturated hydrocarbons is introduced by 5 to the extractive distillation column 10. The solvent is fed near the top of the extractive distillation column 10 by 15 to assure its presence in high concentration upon most of the trays. The solvent alters the relative volatility of the original constituents, allowing separation of the feed into column overhead comprising olefinically unsaturated hydrocarbon or hydrocarbons of the mixture and extract comprising essentially diolefinically unsaturated hydrocarbon or hydrocarbons of the mixture and the solvent. The distillation conditions which are maintained to permit the separation include proper temperature, which is achieved by heat from the column reboiler 20, and proper pressure. The column overhead stream, withdrawn from the extractive distillation column 10 via 25, is passed into column condenser 30, where it is cooled and condensed. From column condenser 30 the condensed column overhead stream is passed to the accumulator 35 via 40. A part of the column overhead stream is withdrawn from the accumulator 35 by 45 and a part thereof is returned as reflux to the extractive distillation column 10 via 50.

The extract stream is withdrawn from the extractive distillation column 10 by 55 and fed to the mid-section of the stripper 60. The operating conditions in the stripper 60, including temperature and pressure, are such as to separate the feed into stripper overhead comprising mainly diolefinically unsaturated hydrocarbon or hydrocarbons and stripper bottoms comprising essentially solvent. The necessary heat is supplied to the stripper 60 by a reboiler 65. The stripper overhead is withdrawn from the stripper 60 by 70 and directed therefrom to a condenser 75 which cools and condenses the stripper overhead stream 70 before it is passed to the accumulator 90. A part of the liquid from the accumulator 90 is returned to the stripper 60 as a reflux stream 100 and a part thereof is withdrawn as product via 105. The stripper bottoms stream withdrawn by 107 is passed through the cooler 108 and then combined with the fresh solvent feed 110 to form solvent feed stream 15.

The following examples are included for illustrative purposes only and are not intended to limit in any way the scope of the invention.

EXAMPLE I

Hydrocarbon feed comprising 50.68 mole percent of butene-1 and 49.32 mole percent of butadiene was introduced into a conventional vapor-liquid equilibration cell, together with selective solvent having molecular weight of 92.05 and comprising 35 weight percent of methylethylketone and 65 weight percent of methylethylsulfone. The following equilibrium data were obtained at stated temperatures and pressures:

1. Temperature = 121° F  Pressure = 19.57 psia

| | Mole fraction in vapor | Mole fraction in liquid | $K_1$ Equilibrium constant-actual | $K_2$ Equilibrium constant-ideal | $K_1/K_2$ | Relative Volatility Butene-1/Butadiene |
|---|---|---|---|---|---|---|
| Air | .0329 | — | — | | | |
| Butene-1 | .5510 | .0293 | 18.817 | 3.952 | 4.76 | 1.904 |
| Butadiene | .3054 | .0309 | 9.885 | 3.816 | 2.59 | |
| MEK | .1107 | .4199 | | | | |
| MES | — | .5199 | | | | |

6.02 mol % HC in liquid
3.69 wt % HC in liquid

2. Temperature = 120° F  Pressure = 49.38 psia

-continued

|  | y | x | $K_{actual}$ | $K_{ideal}$ | $K_1/K_2$ | Relative Volatility Butene-1/ Butadiene |
|---|---|---|---|---|---|---|
| Air | .0156 | — | — | — | — | — |
| Butene-1 | .5959 | .1155 | 5.158 | 1.613 | 3.20 | 1.692 |
| Butadiene | .3563 | .1169 | 3.048 | 1.554 | 1.96 |  |
| MEK | .0322 | .3430 |  |  |  |  |
| MES |  | .4246 |  |  |  |  |

23.24 mol % HC in liquid
15.34 wt % HC in liquid

3. Temperature = 119° F  Pressure = 63.28 psia

|  | y | x | $K_{actual}$ | $K_{ideal}$ | $K_1/K_2$ | Relative Volatility Butene-1/ Butadiene |
|---|---|---|---|---|---|---|
| Air | .0076 | — | — | — | — | — |
| Butene-1 | .5898 | .1954 | 3.019 | 1.269 | 2.38 | 1.527 |
| Butadiene | .3826 | .1934 | 1.978 | 1.220 | 1.62 |  |
| MEK | .0200 | .2731 |  |  |  |  |
| MES | — | .3381 |  |  |  |  |

38.88 mol % HC in liquid
27.58 % HC in liquid

4. Temperature = 119° F  Pressure = 67.53 psia

|  | y | x | $K_{actual}$ | $K_{ideal}$ | $K_1/K_2$ | Relative Volatility Butene-1/ Butadiene |
|---|---|---|---|---|---|---|
| Air | .0107 | — | — | — | — | — |
| Butene-1 | .5800 | .2323 | 2.497 | 1.196 | 2.09 | 1.454 |
| Butadiene | .3924 | .2285 | 1.717 | 1.150 | 1.49 |  |
| MEK | .0169 | .2409 |  |  |  |  |
| MES | — | .2983 |  |  |  |  |

46.08 mol % HC in liquid
33.85 wt % HC in liquid

From the data obtained, it can be concluded that a mixture of butene-1 and butadiene can be separated into its constituent components by extractive distillation with a selective solvent which comprises 65 weight percent of methylethylsulfone and 35 weight percent of methylethylketone. The relative volatility of butene-1/butadiene, altered by the selective solvent ranges from 1.454 at temperature of 119° F (48° C) and pressure of 67.53 psia to 1.904 at temperature of 121° F (50° C) and pressure of 19.57 psia.

EXAMPLE II

The following example was calculated for a system similar to that depicted in the FIGURE. The conditions of the specific pieces of equipment are as follows:

4. Temperature = 119° F  Pressure = 67.53 psia

|  | y | x | $K_{actual}$ | $K_{ideal}$ | $K_1/K_2$ | Relative Volatility Butene-1/ Butadiene |
|---|---|---|---|---|---|---|
| Air | .0107 | — | — | — | — | — |
| Butene-1 | .5800 | .2323 | 2.497 | 1.196 | 2.09 | 1.454 |
| Butadiene | .3924 | .2285 | 1.717 | 1.150 | 1.49 |  |
| MEK | .0169 | .2409 |  |  |  |  |
| MES | — | .2983 |  |  |  |  |

46.08 mol % HC in liquid
33.85 wt % HC in liquid

|  | Temperature | Pressure |
|---|---|---|
| Extractive distillation column* | 110° F (43° C)** | 85 psia (585 kPa) |
| Top of the column |  |  |
| Bottom of the column |  |  |
| Stripper |  | 70 psia (482 kPa) |
| Top of the stripper | 100° F (38° C) |  |
| Bottom of the stripper | 325° F (163° C) |  |

*60 theoretical stages; reflux ratio about 2.7
** average temperature

|  | Extractive Distillation Column | | Stripper | |
|---|---|---|---|---|
|  | Feed kg | Overhead kg | Solvent kg | Overhead kg |
| Butene-1 | 21.0 | 20.9 |  | 0.1 |
| Butadiene | 60.0 | 0.0 |  | 60.0 |
| n-Butane | 5.0 | 5.0 |  | 0.0 |
| t-Butene-2 | 9.0 | 6.0 |  | 3.0 |
| C-Butene-2 | 4.8 | 0.0 |  | 4.8 |
| Vinylacetylene | 0.2 | 0.0 |  | 0.2 |
| Solvent* |  |  | 500.0 | 500.0 |
| Totals | 100.0 | 31.9 | 500.0 | 68.1 |

*35 weight percent methylethylketone, 65 weight percent methylethylsulfone

This example indicates that a mixture of methylethylketone and methylethylsulfone can be used as an extractive solvent in an extractive distillation process for separation of butene-1 from butadiene.

Although selective solvents of this invention have been described in connection with a process for separation of olefins from diolefins, these are also useful as extractive distillation solvents for separation of paraffins and olefins. In such application, the preferred solvent composition will be in the same composition range as for olefin-diolefin separation, but will be relatively leaner in methylethylketone to obtain the most economical hydrocarbon solubility level.

I claim:

1. A process for separating a mixture containing olefins and diolefins which comprises:
   a. introducing the mixture together with a selective solvent comprising methylethylsulfone and at least one solvent modifier selected from the group including methylethylketone, acetone, and tetrahydrofuran into a fractionation zone having a top and a bottom and therein subjecting the mixture, methylethylsulfone and the solvent modifier to extractive distillation conditions including such pressure and corresponding temperature to separate these into a column overhead containing substantially all olefin and an extract bottoms containing mainly diolefin and the selective solvent; and
   b. withdrawing a column overhead stream containing substantially all olefin and an extract bottoms stream containing mainly diolefin and the selective solvent.

2. A process as claimed in claim 1 wherein said olefin is butene-1 and said diolefin is butadiene.

3. A process as claimed in claim 1 further comprising separating diolefin from the extract bottoms stream, and recycling the olefin free extract bottoms stream to the fractionation zone.

4. A process as claimed in claim 1 wherein the weight ratio of the selective solvent to the mixture is from about 2.0 to about 8.0.

5. A process as claimed in claim 1 wherein the selective solvent comprises about 55–85 weight percent of methylethylsulfone and about 15–45 weight percent of methylethylketone.

6. A process as claimed in claim 1 wherein the selective solvent comprises about 65–90 weight percent of methylethylsulfone and about 10–35 weight percent of acetone.

7. A process as claimed in claim 1 wherein the selective solvent comprises about 55–85 weight percent of methylethylsulfone and about 15–45 weight percent of tetrahydrofuran.

8. A process as claimed in claim 3 wherein the pressure in said fractionation zone is from about 55 psia to about 115 psia and the corresponding temperature range is from about 80° F to about 140° F in the top of the fractionation zone, and from about 210° F to about 250° F in the bottom of the fractionation zone.

9. A process as claimed in claim 1 further comprising:
   passing the extract bottoms stream into a stripping zone and therein maintaining such conditions including temperature and pressure as to separate the extract bottoms stream into stripper overhead containing mainly diolefin and stripper bottoms containing essentially selective solvent;
   removing a stripper overhead stream and a stripper bottoms stream;
   cooling the stripper bottoms stream; and
   recycling the cooled stripper bottoms stream to the fractionation zone.

10. A process as claimed in claim 9 wherein the pressure in said stripping zone is from about 55 psia to about 115 psia and the corresponding temperature range is from about 80° F to about 140° F in the top of the stripping zone, and from about 270° F to about 340° F in the bottom of the stripping zone.